United States Patent [19]
Martinez

[11] Patent Number: 6,099,871
[45] Date of Patent: *Aug. 8, 2000

[54] ANTI-REGURGITATION INFANT FORMULA

[75] Inventor: Sarah B. Martinez, Newburgh, Ind.

[73] Assignee: Bristol-Myers Squibb Company, Princeton, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/637,158

[22] Filed: May 3, 1996

Related U.S. Application Data

[63] Continuation-in-part of application No. 08/457,699, Jun. 1, 1995, abandoned.

[51] Int. Cl.$^7$ ...................................................... A23C 9/00
[52] U.S. Cl. .............................. 426/2; 426/578; 426/661; 426/801
[58] Field of Search ............................... 426/2, 578, 661, 426/801

[56] References Cited

U.S. PATENT DOCUMENTS

| | | |
|---|---|---|
| 3,539,358 | 11/1970 | Hing . |
| 4,140,760 | 2/1979 | Withington ............................... 424/81 |
| 4,414,238 | 11/1983 | Schmidl ................................... 426/602 |
| 4,428,972 | 1/1984 | Wurzburg ................................ 426/578 |
| 4,670,268 | 6/1987 | Mahmoud ................................ 426/72 |
| 4,743,682 | 5/1988 | Lee . |
| 4,830,861 | 5/1989 | Puski et al. . |
| 4,990,344 | 2/1991 | Euber et al. . |
| 5,234,706 | 8/1993 | Simak . |

FOREIGN PATENT DOCUMENTS

| | | |
|---|---|---|
| 0 611 525 | 8/1994 | European Pat. Off. . |
| 948361 | of 1982 | U.S.S.R. . |
| 1301371 | of 1987 | U.S.S.R. . |
| 1220838 | 1/1971 | United Kingdom . |
| WO 96/27368 | 9/1996 | WIPO . |

OTHER PUBLICATIONS

Database WPI, Section Ch, Week 9315, Derwent Publications Ltd., London, GB; Class D12, AN 93–124523, Apr. 30, 1992.
Vandenplas, Y. et al., "Milk–thickening Agents as a Treatment for Gastroesophageal Reflux", *Clinical Pediatrics*, 1987, 26(2), 66–68.
Orenstein, S.R., "Thickening of Infant Feedings for Therapy of Gastroesophageal Reflux", *J. of Pediatrics*, 1987, 110(2), 181–186.
Vandenplas, Y., "A Clinical Trial with an 'Anti–regurgitation' Formula", *Eur. J. Pediatr.*, 1994 153, 419–423.
Abstract for: Gitzelmann, R. et al, *Eur. J. Pediatrics*, 1986, 145(2) 504–6.
Abstract for: Dabrowska, W. et al., *Przeglad Mleczarski*, 1978, 27(4), 17–19.
Abstract for: Pouiot, Y. et al., *Food Structure*, 1990, 9(1), 1–8.
Abstract for: Hasselstrom, E., *Deutsche Molkeri–Zeitung*, 1980, 101(35), 1282–1283.
Abstract for: Kersting, M. et al., *Ernaehrungs–Umschau*, 1988, 35(6), 203–206, 208–211,202.
Abstract for: Fatin, J.R., *Lait*, 1969, 49(483/484), 207–11.
Abstract for: Pordab, Z., *Przemysl Spozywcyzy*, 1975, 29(12), 477.
Infant Formula Act of 1980, Sep. 26, 1980, Public Law 96–356, Food Drug Cosmetic Law Reports, ¶ 653—¶ 671.
Nestlé Beba® German Product Literature, No date.
Nestlé Beba® 2 German Product Literature No date.
Nestlé Beba® 1 German Product Literature, No date.
Nestlé Beba® H.A. 2 German Product Literature, No date.
Nestlé Beba®H.A. 1 German Product Literature, No date.
Karicare™ Food Thickener, No date.

*Primary Examiner*—Lien Tran
*Attorney, Agent, or Firm*—Judith A. Roesler; Wendell Ray Guffey

[57] ABSTRACT

Infant formula containing certain thickening agents useful for treating regurgitation. The thickening agent can be waxy corn starch, waxy rice starch, or a mixture thereof.

47 Claims, No Drawings

ANTI-REGURGITATION INFANT FORMULA

This is a continuation-in-part of Ser. No. 08/457,699 filed Jun. 1, 1995 now abandoned.

FIELD OF INVENTION

The present invention concerns infant formula thickened with a potato starch or waxy starch which contains a high level of amylopectin.

BACKGROUND OF INVENTION

Starch is composed of two distinct polymer fractions: amylose and amylopectin. Amylose is the linear fraction consisting of α-1,4 linked glucose units. Amylopectin has the same structure as amylose but some of the glucose units are combined in an α-1,6 linkage giving rise to a branched structure. Starches generally contain 17–24% amylose and from 76–83% amylopectin.

Special genetic varieties of plants have been discovered or developed which produce starch with unusual amylose to amylopectin ratios. Some plants produce starch that is free of amylose. These mutants produce starch granules in the endosperm and pollen which stain red with iodine and which contain nearly 100% amylopectin. Predominant among such amylopectin producing plants are waxy corn, waxy sorghum and waxy rice starch.

Regurgitation of infant formula by infants is a common problem. The addition of certain thickening agents to infant formulas is known in the art to be effective in reducing the incidence and/or severity of regurgitation. Examples of thickening agents known in the art include rice cereal (see, Ramenofsky, M. L., et al, *J. Pediatr. Surg,* 1981; 16:374–378) and seed gums like carob bean gum (see, Vandenplas, Y., et al, *Clin. Pediatics,* 1987; 26(2):66–68; European Patent 0611524).

Commercial products are Frisovom from Friesland Frico Domo and Nutrilon AR from Nutricia which contain locust bean gum as a thickening agent.

It has been discovered that use of potato starch or certain high amylopectin containing grain starches in infant formulas provides advantages heretofore unachievable.

SUMMARY OF INVENTION

The present invention is directed to an infant formula comprising a thickening agent which comprises potato starch, waxy grain starch, or mixtures thereof in an amount effective to ameliorate regurgitation in infants.

In another aspect, the present invention is directed to a method for treating regurgitation in an infant in need of treatment comprising administering to said infant an effective amount of the infant formula of the invention.

DETAILED DESCRIPTION OF INVENTION

The present invention provides an infant formula thickened with certain food starches for the management of postprandial gastroesophageal reflux ("GER", commonly referred to as "regurgitation"). To thicken the infant formula, starches derived from the following sources can be used alone or in combination: potato starch or waxy grain starch. The infant formula so thickened has been found to be advantageous in the treatment of regurgitation.

The starches can be used in their native state or with additional pre-treatments such as pregelatinization or agglomeration to facilitate ease of use. By the term "waxy" it is meant an appropriate starch which contains at least about 90% amylopectin by weight. Preferred waxy starches contain at least about 95% amylopectin and more preferred starches contain at least about 98% amylopectin by weight.

Preferred waxy starches are waxy corn, waxy rice and waxy sorghum. More preferred are waxy corn and waxy rice, and most preferred is waxy rice.

Waxy corn starch has an amylopectin content of approximately 99%. Rice flour has slightly lower viscosity than rice starch for non-waxy samples; however, twice as much waxy rice flour is needed to obtain the same viscosity as given by waxy rice starch. Waxy rice starch has 98–100% amylopectin. Rice has one of the smallest starch granules of the cereal starches, varying in size from about 3–10 micrometers ($\mu$m) in the mature grain. Mean granule size varies from about 4–6 $\mu$m. Potato starches have generally larger granules than the grain starches, e.g., about 30–50 $\mu$m. When cooked, the large swollen granules impart extra high viscosity.

Prior art formulas using rice cereal as a thickening agent become hypercaloric. Such prior art formulas can have caloric densities of up to 30 Calories per fluid ounce (Cal./fl. oz.). In contrast, the formula of the invention is not hypercaloric, i.e., has a caloric density of not more than 24 Cal./fl. oz., preferably not more than 20 Cal./fl. oz. The present invention specifically contemplates formulas having a caloric density greater than 20 Cal./fl. oz. and not more than 24 Cal./fl. oz.

Rice cereal or gums could also make the formula too thick so that the infant would have to work hard at sucking out of the normal hole in a bottle nipple. This is usually remedied by cutting bigger holes in bottle nipples but could cause the formula to flow too quickly, which may lead to choking and tongue thrusting in an infant already at risk for oral motor dysfunction. Moreover, rice cereal is not soluble and has a tendency to settle, resulting in instability upon storage. Rice flour has slightly lower viscosity than rice starch for non-waxy samples; however, twice as much waxy rice flour is needed to obtain the same viscosity as given by waxy rice starch.

The performance of starches of the invention under conditions of heat, shear and acid may be improved by chemical modifications. Modifications are usually attained by introduction of substituent chemical groups. Viscosity at high temperatures or high shear can be increased or stabilized by cross-linking with di- or polyfunctional reagents such as phosphorus oxychloride.

In some instances, it is preferred that the starch of the invention is pregelatinized. Pregelatinization of starch is a process of precooking starch to produce material that hydrates and swells in cold water. Drum drying is the most common method of preparation. The feed starch can be a chemically modified product to further extend the range of finished properties.

Native starch granules are insoluble in water but when heated in water, the granule begins to swell when sufficient heat energy is present to overcome the bonding forces of the starch molecules. With continued heating, the granule swells to many times its original volume. The friction between these swollen granules is the major factor that contributes to starch paste viscosity.

Prior art formulas using non-waxy starches as a thickening agent are hypercaloric formulas. Also, such non-waxy starches usually are not pregelatinized.

Prior art formulas using seed gums like carob or locust bean gum as thickening agents result in instability upon storage in that they tend to separate into two phases when allowed to stand. Also, such products become overly thick necessitating cutting bigger holes in bottle nipples.

In contrast to prior art formulas, the infant formula of the present invention has excellent storage stability and is not hypercaloric. The infant formula of the invention is also a calorically balanced formula. By the term "calorically balanced" is meant that the calories from protein, fat and carbohydrate are in proportions similar to human milk. The viscosity of normal infant formula is about 5–10 centipoise (cp). The viscosity of the formula of the invention is sufficiently high (e.g., about 30 to about 300 cp, preferably about 35 to about 150 cp) to be effective in treating regurgitation, but not so high as to inhibit pourability.

Viscosity is measured by using a Brookfield viscomer with a number 1 spindle at 60 rpm at 30° C.

By the use of the starches of the invention, e.g., waxy corn starch, waxy rice starch, and/or potato starch in accordance with the present invention, it is possible to use much less starch (e.g., in the range of 75% or less) to achieve anti-regurgitation effects than prior art starch, such as non-waxy corn starch. Thus, the caloric content of the infant formula of the invention is optimized to be not hypercaloric and is most preferably approximately the same (20 Cal./fl. oz.) as commercial infant formulas such an Enfamil® (available from Mead Johnson and Company, Evansville, Ind.).

An "effective" amount of the infant formula of this invention is an amount sufficient to result in ameloriation of regurgitation. By the term "ameloriation" is meant prevention or any reduction in severity or incidence of regurgitation in an infant ingesting the formula of the invention as compared with ingesting of the same formula without the required starch (the carbohydrate component of such a control formula would be made up with common non-polymer sugars, such as lactose, glucose, or sucrose).

It is preferred that the infant formula of the invention is nutritionally complete. By the term "nutritionally complete" is meant that the composition contains adequate nutrients to sustain healthy human life for extended periods. The infant formula of the invention contains ingredients which are designed to meet the nutritional needs of the human infant namely, a protein, carbohydrate and lipid source and other nutrients such as vitamins and minerals.

The amount of protein per 100 Cal. of total formula is typically about 1.8 g to about 4.5 g; the amount of lipid source per 100 Cal. of total formula is typically about 3.3 g to about 6 g; and the amount of carbohydrate source per 100 Cal. of total formula is typically about 7 g to about 14 g.

The protein source can be non-fat milk solids, a combination of non-fat milk solids and whey protein, a partial hydrolysate of non-fat milk and/or whey solids, soy protein isolates, or partially hydrolyzed soy protein isolates. The infant formula can be casein predominant or whey predominant.

The carbohydrate source in the infant formula (other than starch) can be any carbohydrate known in the art to be suitable for use in infant formulas. Typical carbohydrate sources include sucrose, fructose, glucose, maltodextrin, lactose, corn syrup, corn syrup solids, and the like.

The infant formula of the present invention contains an amount of starch of the invention (e.g., waxy corn, waxy rice and/or potato starch) in an amount effective to ameloriate regurgitation.

Such an amount is typically about 1.8 to about 5 g of starch per 100 Cal. of formula; preferred is about 2 to about 4.7 g of starch per 100 Cal. of formula; more preferred is about 2 to about 3 g of starch per 100 Calories of formula.

The lipid source in the infant formula can be any lipid or fat known in the art to be suitable for use in infant formulas. Typical lipid sources include milk fat, safflower oil, egg yolk lipid, olive oil, coconut oil, palm oil, palm kernel oil, soybean oil, sunflower oil, fish oil and fractions derived thereof such as palm olein, medium chain triglycerides (MCT), and esters of fatty acids wherein the fatty acids are, for example, arachidonic acid, linoleic acid, palmitic acid, stearic acid, docosahexaenoic acid, eicosapentaenoic acid, linolenic acid, oleic acid, lauric acid, capric acid, caprylic acid, caproic acid, and the like. High oleic forms of various oils are also contemplated to be useful herein such as high oleic sunflower oil and high oleic safflower oil. Medium chain triglycerides contain higher concentrations of caprylic and capric acid than typically found in conventional oils, e.g., approximately three-fourths of the total fatty acid content is caprylic acid and one-fourth is capric acid.

Nutritionally complete compositions contain all vitamins and minerals understood to be essential in the daily diet and these should be present in nutritionally significant amounts. Those skilled in the art appreciate that minimum requirements have been established for certain vitamins and minerals that are known to be necessary for normal physiological function. Practitioners also understand that appropriate additional amounts (overages) of vitamin and mineral ingredients need to be provided to compensate for some loss during processing and storage of such compositions.

To select a specific vitamin or mineral compound to be used in the infant formula of the invention requires consideration of that compound's chemical nature regarding compatibility with the particular processing conditions used and shelf storage.

Examples of minerals, vitamins and other nutrients optionally present in the composition of the invention include vitamin A, vitamin $B_6$, vitamin $B_{12}$, vitamin E, vitamin K, vitamin C, folic acid, thiamine, inositol, riboflavin, niacin, biotin, pantothenic acid, choline, calcium, phosphorus, iodine, iron, magnesium, copper, zinc, manganese, chloride, potassium, sodium, selenium, chromium, molybdenum, taurine, and L-carnitine. Minerals are usually added in salt form. In addition to compatibility and stability considerations, the presence and amounts of specific minerals and other vitamins will vary somewhat depending on the intended infant population.

The infant formula of the invention also typically contains emulsifiers and stabilizers such as soy lecithin, carrageenan, and the like.

The infant formula of the invention may optionally contain other substances which may have a beneficial effect such as lactoferrin, nucleotides, nucleosides, immunoglobulins, and the like.

The infant formula of the invention is in concentrate liquid form, liquid ready to consume form, or powder form. Of course, if in powder form, the formula is diluted to normal strength with water to be in a form ready to consume.

The osmolality of the liquid infant formula of the invention (when ready to consume) is typically about 100 to 500 mOsm/kg $H_2O$, more typically about 200 to 400 mOsm/kg $H_2O$.

The infant formula of the invention is shelf stable after reconstitution. By "shelf stable" is meant that the formula in a form ready to consume remains in a single homogenous phase (i.e., does not separate into more than one phase upon visual inspection) or that the thickener does not settle out as a sediment upon visual inspection after storage overnight in the refrigerator. With the thickened nature of the product, the formula of the invention also has the advantage of remaining fluid (i.e., does not gel into a solid mass when stored overnight in the refrigerator).

In the method of the invention, tile infant formula is administered to an infant. The form of administration is oral, which includes tube feeding.

Aside from ameliorating regurgitation, such as reducing the episodes of regurgitation, it is also preferred that the formula of the invention decreases the number and total volume of emesis, decreases crying time and increases sleep time in the postprandial period. It is also preferred that the formula of the invention reduces the percentage of time that esophageal pH is <4.0 in infants with gastrooesophageal reflux.

The invention is further illustrated by the following examples, which should not be interpreted as a limitation thereon (percentages are by weight unless otherwise indicated):

EXAMPLE 1

Anti-Regurgitation Formula of the Invention

|  | Per 100 Cal. |
|---|---|
| Food Energy, Cal. | 100 |
| Protein,[1] g | 3.3 |
| Fat,[2] g | 4.4 |
| Carbohydrate,[3] g | 11.8 |
| Minerals (ash, g) | 0.75 |
| Water, g | — |
| Vitamin A, IU | 300 |
| Vitamin D, IU | 60 |
| Vitamin E, IU | 2 |
| Vitamin K, mcg | 8 |
| Thiamine, mcg | 80 |
| Riboflavin, mcg | 150 |
| Vitamin $B_6$, mcg | 90 |
| Vitamin $B_{12}$, mcg | 0.3 |
| Niacin, mcg | 1000 |
| Folic Acid, mcg | 16 |
| Pantothenic Acid, mcg | 500 |
| Biotin, mcg | 3 |
| Vitamin C, mg | 12 |

-continued

|  | Per 100 Cal. |
|---|---|
| Choline, mg | 12 |
| Inositol, mg | 6 |
| Taurine, mg | 6 |
| Calcium, mg | 116 |
| Phosphorus, mg | 92 |
| Magnesium, mg | 11 |
| Iron, mg | 1.8 |
| Zinc, mg | 1 |
| Manganese, mcg | 15 |
| Copper, mcg | 75 |
| Iodine, mcg | 8 |
| Sodium, mg | 49 |
| Potassium, mg | 150 |
| Chloride, mg | 100 |
| Linoleic Acid, g | 0.72 |
| Linolenic Acid, mg | 75 |

[1]Nonfat milk solids or a combination of whey and nonfat milk solids.
[2]Palm olein oil, soy oil, coconut oil, and high oleic sunflower oil.
[3]57% Lactose, 30% waxy rice starch, 13% corn syrup solids.

EXAMPLE 2

Anti-Regurgitation Formula of the Invention

|  | Per 100 Cal. |
|---|---|
| Food Energy, Cal. | 100 |
| Protein,[1] g | 2.5 |
| Fat,[2] g | 5.1 |
| Carbohydrate,[3] g | 11.0 |
| Minerals (ash, g) | 0.6 |
| Water, g | — |
| Vitamin A, IU | 300 |
| Vitamin D, IU | 60 |
| Vitamin E, IU | 2 |
| Vitamin C, mg | 12 |
| Folic Acid, mcg | 16 |
| Thiamine, mcg | 80 |
| Riboflavin, mcg | 90 |
| Niacin, mcg | 1000 |
| Vitamin $B_6$, mcg | 60 |
| Vitamin $B_{12}$, mcg | 0.30 |
| Biotin, mcg | 3.0 |
| Pantothenic Acid, mcg | 500 |
| Vitamin K, IU | 8 |
| Choline, mg | 12 |
| Calcium, mg | 82 |
| Phosphorus, mg | 65 |
| Iodine, mcg | 15 |
| Iron, mg | 1.13 |
| Magnesium, mg | 8.0 |
| Zinc, mg | 1.0 |
| Copper, mcg | 65 |
| Manganese, mcg | 10 |
| Sodium, mg | 35 |
| Potassium, mg | 125 |
| Chloride, mg | 80 |
| Taurine, mg | 6 |
| Linoleic acid, g | 0.86 |
| Linolenic Acid, mg | 90 |

[1]Nonfat milk solids or a combination or whey and nonfat milk solids.
[2]Palm olein oil, soy oil, coconut oil, and high oleic sunflower oil.
[3]44% Lactose, 29% waxy rice starch, 27% corn syrup solids.

EXAMPLE 3

Process for Preparing an Anti-Regurgitation Formula of the Invention

For an anti-regurgitation infant formula powder, such as in Example 1 or 2, to the non-fat milk is added lactose and 5 minerals dissolved beforehand. The mixture is heated to 70° C. in a plate type heat exchanger. This is followed by the introduction of fats which consist of palm olein, sunflower oil, coconut oil, soy oil, lecithin, mono- and diglycerides and fat soluble vitamins. The oils are melted before addition to the mixture. After preheating to about 75° C., the resulting mixture is homogenized in two stages, first at 125 bar and then at 50 bar. The powder base may be evaporated to 40–50% solids prior to spray drying. To the powder base is dry blended the starch (e.g., waxy corn, waxy rice, and/or potato), additional lactose or corn syrup solids and the vitamins and minerals. Soy protein isolate can be substituted for non-fat milk and corn syrup solids can be substituted for lactose.

EXAMPLE 4

Process for Preparing an Anti-Regurgitation Formula of the Invention

For another anti-regurgitation infant formula powder, a procedure as in Example 3 is used except that a partial hydrolysate of non-fat dry milk and whey is used instead of the intact protein.

EXAMPLE 5

Process for Preparing an Anti-Regurgitation Formula of the Invention

For an anti-regurgitation infant formula powder, a procedure as in Examples 3 and 4 is used except that the starch is added during the liquid blending of the powder base.

EXAMPLE 6

Process for Preparing an Anti-Regurgitation Formula of the Invention For a liquid anti-regurgitation infant formula, a procedure as in Examples 3 and 4 is used except that the product is diluted to an equivalent of 20 Calories/oz. and sterilized in conventional retort or aseptic systems.

EXAMPLE 7

Comparison of the Infant

Formula of the Invention with Prior Art Infant Formulas[1]

| Thickener (Formula Product Form) | Viscosity (cp) | Amt. of Thickener (g/100 ml formula) |
| --- | --- | --- |
| Waxy rice starch, native, pregelatinized (Powder) | 73 | 2.3 |
| Waxy rice starch, modified, pregelatinized (Powder) | 61 | 2.3 |
| Waxy rice starch, native (Liquid "Ready to Use") | 100–150 | 2.0 |
| Waxy corn, native, pregelatinized (Powder) | 30.7 | 2.0 |
| Potato starch (Powder) | 40 | 2.0 |
| Waxy rice starch, native, pregelatinized (Powder, partially hydrolyzed protein based formula) | 48.5 | 2.3 |
| Waxy rice starch, native, pregelatinized (Powder, soy-based formula) | 55.2 | 2.3 |

[1]Formulas similar to reconstituted Example 1 with the indicated type of thickeners.

Commercial Products

| BRAND (Manufacturer) | DESCRIPTION | VISCOSITY (cp) | AMT. OF THICKENER (g/100 ml) | CHARACTERISTICS OF FORMULA |
| --- | --- | --- | --- | --- |
| Nutrilon AR (Nutricia N.V.) | Milk-based infant formula w/ carob gum | 70–200 | 0.4 | Separates into curdy particles and a serum layer when allowed to stand. Variable viscosity. |
| Nutrilon AR Plus (Nutricia N.V.) | Follow-on milk-based infant formula w/ carob gum | 70–200 | 0.4 | Separates into curdy particles and a serum layer when allowed to stand. Variable viscosity. |
| Frisovom (Friesland Frico Domo) | Milk based infant formula w/ carob gum | 65.6 | 0.8 | Separates into curdy particles and a serum layer when allowed to stand. |
| Nestargel (Nestle) | Carob gum preparation added to infant formula | 355 | *1.0 | |
| Karicare Food Thickener (Douglas Pharmaceuticals Australia Ltd) | Pregelatinized corn starch added to infant formula | 43 | *3.9 | Formula is hypercaloric: additional 15 calories/100 ml |
| Gelopectose (Nutripharm Elgi) | Pectin/microcrystalline cellulose added to infant formula | 40–50 | *5.0 | Gels when stored in refrigerator |
| Gummilk | Carob gum added to infant | 487 | *2.0 | Formula barely pourable. Gels |

-continued

Commercial Products

| BRAND (Manufacturer) | DESCRIPTION | VISCOSITY (cp) | AMT. OF THICKENER (g/100 ml) | CHARACTERISTICS OF FORMULA |
|---|---|---|---|---|
| (Gallia) | formula | | | when stored in refrigerator. |
| | Rice cereal added to infant formula | 800 | 8.0 | Formula is hypercaloric: additional 10 calories/100 ml. Cereal settles out. Bottle nipple needs to be enlarged. |

*Added to formula per label instructions.

What is claimed is:

1. An infant formula comprising a waxy grain starch thickening agent in an amount effective to ameliorate regurgitation in infants wherein said formula has a caloric density of not more than 24 Cal./Fl. oz.

2. The infant formula of claim 1 wherein the effective amount of thickening agent is about 1.8 to 5 g per 100 Calories of formula.

3. The infant formula of claim 1 wherein the effective amount of thickening agent is about 2 to about 4.7 g per 100 Calories of formula.

4. The infant formula of claim 1 wherein the effective amount of thickening agent is about 2 to about 3 g per 100 Calories of formula.

5. The infant formula of claim 1 wherein said thickening agent is selected from the group consisting of waxy rice starch, waxy corn starch, or a mixture thereof and said caloric density is not more than about 20 Cal./Fl. oz.

6. The infant formula of claim 5 wherein said waxy rice starch or waxy corn starch comprises at least about 95% amylopectin by weight.

7. The infant formula of claim 5 wherein said waxy rice starch or waxy corn starch comprises at least about 98% amylopectin by weight.

8. The infant formula of claim 5 wherein said thickening agent is waxy rice starch wherein the effective amount of thickening agent is from about 2 to about 3 g per 100 Calories of formula.

9. The infant formula of claim 1 having a Brookfield viscosity of about 35 to about 150 cp, wherein said thickening agent is a waxy grain starch selected from the group consisting of waxy rice starch, waxy corn starch, waxy sorghum starch, and a mixture thereof.

10. The infant formula of claim 1 wherein said formula does not separate into two phases or gel into a solid mass when prepared in a form to feed and is stored overnight in the refrigerator.

11. The infant formula of claim 1 comprising, per 100 Kcal of total formula, about 1.8 g to about 4.5 g protein, about 3.3 g to about 6 g lipid, about 7 g to about 14 g carbohydrate, and from about 1.8 to 5 g of said thickening agent.

12. The infant formula of claim 11 further comprising vitamins and minerals, wherein said thickening agent is a waxy rice starch and said formula has a caloric density not more than about 20 Cal./Fl. oz.

13. The infant formula of claim 1 further comprising nutrients in an amount sufficient to sustain healthy human life for an extended period.

14. An infant formula of claim 1 wherein said formula has a caloric density of not more than 20 Cal./Fl. oz. and when constituted as a liquid, the osmoality of said infant formula is from about 200 to about 400 mOsm/kg $H_2O$.

15. The infant formula of claim 1 which has a caloric density of not more than 20 Cal./fl. oz.

16. The infant formula of claim 1 which has a caloric density of greater than 20 Cal./fl. oz. and not more than 24 Cal./fl. oz.

17. The infant formula of claim 1 wherein said formula has calories from protein, fat and carbohydrate proportions similar to human milk.

18. A method of treating regurgitation in an infant in need of treatment comprising administering to said infant an effective amount of an infant formula comprising a waxy grain starch thickening agent in an amount effective to ameliorate regurgitation in infants.

19. The method of claim 18 wherein the effective amount of thickening agent is about 2 to about 4.7 g per 100 calories of formula.

20. The method of claim 18 wherein said thickening agent is selected from the group consisting of waxy rice starch, waxy corn starch, or a mixture thereof.

21. The method of claim 18 wherein said thickening agent is selected from the group consisting of waxy rice starch or waxy corn starch and said starch comprises at least about 98% amylopectic by weight.

22. The method of claim 18 wherein said infant formula is in a form ready to use and does not separate into two phases nor gel into a solid mass when stored overnight in the refrigerator.

23. The method of claim 18 wherein said infant formula comprises, per 100 Kcal of total formula, about 1.8 g to about 4.59 g protein, about 3.3 g to about 6 g lipid, and about 7 g to about 14 g carbohydrate, and further comprises vitamins and minerals.

24. The method of claim 23 wherein said infant formula further comprises nutrients in an amount sufficient to sustain healthy human life for an extended period.

25. The method of claim 18 wherein said infant formula is not hypercaloric.

26. The method of claim 18 wherein said infant formula has a caloric density of not more than 20 Cal./fl. oz.

27. The method of claim 18 wherein said infant formula has a caloric density of greater than 20 Cal./fl. oz. and not more than 24 Cal./fl. oz.

28. The infant formula of claim 18 wherein said formula has calories from protein, fat and carbohydrate in proportions similar to human milk.

29. An infant formula comprising a thickening agent comprising at least one waxy grain starch component containing at least about 95% amylopectin content in an amount effective to ameliorate regurgitation in infants wherein said formula has a caloric density of not more than 24 Cal./Fl. oz. and said formula stains red with iodine.

30. The infant formula of claim 29 wherein said waxy starch is pregelatinized.

31. The infant formula of claim 29 wherein said formula has a caloric density of not more than about 20 Cal./Fl. oz. and said waxy starch component is present in an amount ranging from 1.8 to 5 g per 100 Calories of formula.

32. The infant formula of claim 29 wherein said formula has a caloric denisty of not more than about 30 Cal./Fl.oz.

33. The infant formula of claim 32 wherein said waxy grain start is a waxy corn starch and is present in an amount ranging from 2 to about 4.7 g per 100 Calories of formula.

34. The infant formula of claim 33 wherein said waxy corn starch comprises at least about 95% by weight amylopectin.

35. The infant formula of claim 34 wherein said waxy corn starch comprises at least about 98% by weight amylopectin.

36. The infant formula of claim 33 having a Brookfield viscosity of about 35 to about 150 cp and after reconstitution, said formula does not separate into two phases or gel into a solid mass when stored overnight in the refrigerator.

37. The infant formula of claim 29 wherein said waxy grain starch is waxy rice starch.

38. The infant formula of claim 37 wherein said waxy rice starch is pregelatinized.

39. The infant formula of claim 38 wherein said formula has a caloric density of about 20 Cal./Fl.oz. and further comprises nutrients in an amount sufficient to sustain healthy human life for an extended period.

40. The infant formula of claim 39 wherein said waxy rice starch comprises at least about 95% by weight amylopectin.

41. The infant formula of claim 40 wherein said waxy rice starch comprises at least about 98% by weight amylopectin.

42. The infant formula of claim 41 wherein said thickener is present in an amount ranging from 1.8 to 5 g per 100 Calories of formula.

43. An infant formula comprising per 100 Kcal of total formula, about 1.8 g to about 4.5 g protein, about 3.3 g to about 6 g lipid, about 7 g to about 14 g carbohydrate, and from about 1.8 to 5 g of a waxy grain starch, to ameliorate regurgitation in infants wherein said formula has a caloric density of not more than 24 Cal./Fl. oz.

44. An infant formula according to claim 43 wherein said waxy grain starch is selected from waxy rice starch, waxy corn starch, waxy sorghum starch, or a mixture thereof.

45. An infant formula according to claim 44 wherein said waxy grain starch has an amylopectin content of at least about 98% by weight and is present in an amount ranging from 2 g to about 4.7 g of starch per 100 Cal of formula.

46. An infant formula according to claim 45 wherein said waxy grain starch is waxy grain starch present in an amount ranging from 2 to 3 g of starch per 100 calories of formula.

47. An infant formula comprising a thickening agent selected from the group consisting of waxy rice starch, waxy corn starch, waxy sorghum starch or a mixture thereof in an amount effective to emeliorate regurgitation in infants. wherein said infant formula stains red with iodine and said formula has a caloric density of not more that 20 Cal./Fl. oz.

* * * * *